United States Patent
Chen et al.

(10) Patent No.: US 9,970,880 B2
(45) Date of Patent: May 15, 2018

(54) APPARATUS FOR MEASURING A CURVATURE OF A THIN FILM AND THE METHOD THEREOF

(71) Applicant: Industrial Technology Research Institute, Hsinchu (TW)

(72) Inventors: Tzung-Te Chen, Taipei (TW);
Hsueh-Hsing Liu, Taipei (TW);
Chun-Wen Chu, New Taipei (TW);
Yi-Keng Fu, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days. days.

(21) Appl. No.: 15/382,748

(22) Filed: Dec. 19, 2016

(65) Prior Publication Data
US 2018/0052115 A1    Feb. 22, 2018

(30) Foreign Application Priority Data
Aug. 19, 2016 (TW) ............................... 105126574 A

(51) Int. Cl.
*G01B 11/00* (2006.01)
*G01N 21/84* (2006.01)
(Continued)

(52) U.S. Cl.
CPC ......... *G01N 21/8422* (2013.01); *G01B 11/24* (2013.01); *G01N 2021/8427* (2013.01); *H01L 22/12* (2013.01)

(58) Field of Classification Search
CPC .......................... G01B 11/2513; G01B 11/255
See application file for complete search history.

(56) References Cited

U.S. PATENT DOCUMENTS 4,452,534 A * 6/1984 Gribanov ............ G01B 11/2441
356/513
4,588,270 A * 5/1986 Tamaki ................ G01B 11/255
351/212
(Continued)

FOREIGN PATENT DOCUMENTS

CN       104949631       9/2015
TW       I357492         2/2012

OTHER PUBLICATIONS

"Office Action of Taiwan Counterpart Application", dated Mar. 28, 2017, p. 1-p. 6.

*Primary Examiner* — Shawn Decenzo
*Assistant Examiner* — Jarreas C Underwood
(74) *Attorney, Agent, or Firm* — JCIPRNET

(57) ABSTRACT

An apparatus for measuring a curvature of a thin film includes a light emitting module, a first optical module, a second optical module, a third optical module, and an image analysis module. The light emitting module emits a single laser to be used as an incident light. The incident light is transmitted through a first optical path provided by the first optical module, then the incident light is guided by the second optical module to be incident to the thin film through a second optical path. A reflected light reflected by the thin film is transmitted through the second optical path, then guided by the third optical module to be transmitted along a third optical path. The image analysis module determines the curvature of the thin film according to the characteristic of the reflected light.

23 Claims, 4 Drawing Sheets

(51) Int. Cl.
   *G01B 11/24*   (2006.01)
   *H01L 21/66*   (2006.01)

(56) References Cited

U.S. PATENT DOCUMENTS

| | | | | |
|---|---|---|---|---|
| 5,633,718 | A | * | 5/1997 | Manning .............. G01B 11/255 356/4.01 |
| 5,912,738 | A | * | 6/1999 | Chason ................ G01B 11/255 356/601 |
| 6,542,249 | B1 | * | 4/2003 | Kofman .............. G01B 11/2513 356/601 |
| 7,990,543 | B1 | * | 8/2011 | Mello ................ G01B 11/2441 356/512 |
| 8,514,408 | B2 | * | 8/2013 | Zettler ................... G01B 11/25 356/612 |
| 8,810,798 | B2 | * | 8/2014 | Zettler ................... H01L 22/12 356/601 |
| 2007/0030493 | A1 | * | 2/2007 | Zettler ................... G01B 11/24 356/612 |
| 2008/0186512 | A1 | * | 8/2008 | Kee ........................ G01B 11/25 356/610 |
| 2010/0315422 | A1 | * | 12/2010 | Andre ................ G01B 11/2513 345/426 |

* cited by examiner

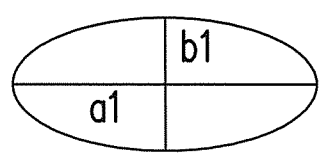
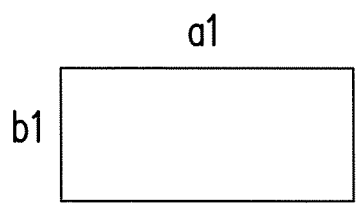
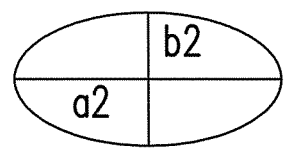
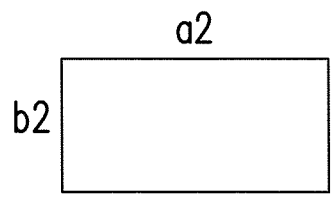
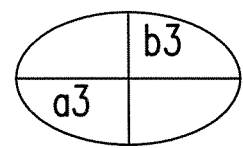
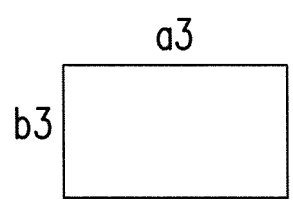
FIG. 5A  FIG. 5B

US 9,970,880 B2

APPARATUS FOR MEASURING A CURVATURE OF A THIN FILM AND THE METHOD THEREOF

CROSS-REFERENCE TO RELATED APPLICATION

This application claims the priority benefit of Taiwan application no. 105126574, filed on Aug. 19, 2016. The entirety of the above-mentioned patent application is hereby incorporated by reference herein.

TECHNICAL FIELD

This disclosure generally relates to an apparatus for measuring a curvature of a thin film, and the method thereof.

BACKGROUND

In the semiconductor epitaxial deposition process, too large lattice mismatch between epitaxial substrate and deposition material, such as gallium nitride (GaN) deposits on a silicon (Si) substrate, will yield intrinsic stress between two materials, and thereby curving the surface of the silicon substrate. Also, lattice mismatch between epitaxial layers in the epitaxial deposition process will yield bending the substrate. Besides, thermal mismatch between layers will yield bending during the fabricating process. The phenomena will reduce the epitaxial quality and affect the fabricating process, thereby increasing the fabricating costs. It results in a need to monitor the curvature variation of the substrate in real time during the epitaxial process and realize the most significant stress is in which layer structure immediately. Therefore, it becomes an important issue for the manufacturers to adjust and control corresponding process parameters to reduce the stress.

SUMMARY

The disclosure provides an apparatus for measuring of a curvature of a thin film. The apparatus includes a light emitting module, a first optical module, a second optical module, a third optical module, and an image analysis module. The light emitting module emits a single laser to be used as an incident light. The first optical module provides a first optical path for the incident light to have a cross-sectional shape of the incident light being a first pattern when the incident light is transmitted through the first optical path. The second optical module provides a second optical path and guides the incident light to be incident to the thin film through the second optical path, and guides a reflected light from the thin film to enter a third optical path, wherein the cross-sectional shape of the reflected light is a second pattern. The third optical module provides a third optical path for the reflected light, to have the reflected light being transmitted through the third optical path. The image analysis module captures the reflected light and analyzes the second pattern, and determines the curvature of the thin film. Wherein the second pattern having at least one characteristic comprises at least one combination of a length variation, a width variation, a ratio variation of length versus width, a ratio variation of major axis versus minor axis and a diagonal variation on different axes.

The disclosure further provides a method for measuring of a curvature of a thin film. First of all, a single laser is emitted to be used as an incident light. The incident light is transmitted through a first optical path, to have a cross-sectional shape of the incident light being a first pattern when the incident light is transmitted through the first optical path. And, the incident light transmitted along the first optical path is guided to be incident to the thin film through a second optical path. Then, a reflected light is guided to enter a third optical path. Wherein the reflected light is reflected from the thin film, and the cross-sectional shape of the reflected light is a second pattern having at least one characteristic. Then, the reflected light is transmitted along the third optical path. The reflected light transmitted to an end of the third optical path is captured. Thereafter, the curvature of the thin film is determined according to the at least one characteristic of the second pattern; wherein the second pattern having the at least one characteristic comprises at least one combination of a length variation, a width variation, a ratio variation of length versus width, a ratio variation of major axis versus minor axis and a diagonal variation on different axes.

The foregoing will become better understood from a careful reading of a detailed description provided herein below with appropriate reference to the accompanying drawings.

BRIEF DESCRIPTION OF THE DRAWINGS

FIGS. 5A and 5B are two groups of single second patterns corresponding to two groups of different standard data, respectively, wherein a single laser is applied and passes through a double slit device, according to one embodiment of the disclosure.

DESCRIPTION OF EMBODIMENTS

Figure 1:
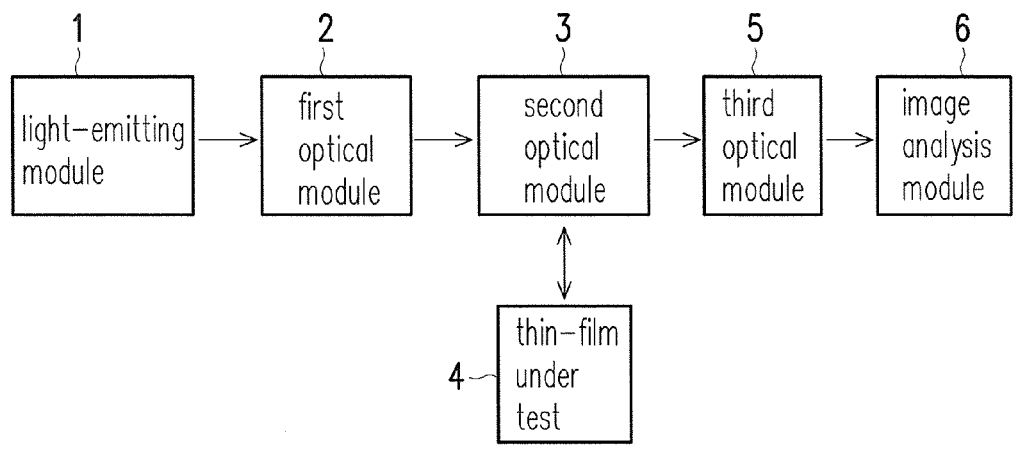
FIG. 1 is a block schematic diagram of an apparatus for measuring a curvature of a thin film according to one embodiment of the disclosure.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

FIG. 1 is a block schematic diagram of an apparatus for measuring a curvature of a thin film according to one embodiment of the disclosure. As shown in FIG. 1, the apparatus for measuring the curvature of the thin film is suitable for measuring the curvature of a thin film 4. The apparatus for measuring the curvature of the thin film includes a light emitting module 1, a first optical module 2, a second optical module 3, a third optical module 5, and an image analysis module 6. The modules 1, 2, 3, 4, and 5 have no substantial connection relationship. The light emitting module 1 emits an incident light which passes through the first optical module 2, the second optical module 3, the thin film 4, and the third optical module 5 in sequence. Accordingly, the relative location relationship among these modules are simply defined.

In this embodiment, the light emitting module 1 of the apparatus for measuring the curvature of the thin film emits a single laser to be used as an incident light. The cross-sectional shape of the incident light is a first pattern. The incident light is transmitted through a first optical path provided by the first optical module 2, and a second optical path provided by the second optical module 3, and then the incident light is guided by the second optical module to be incident to the thin film 4. Next, the thin film 4 reflects the incident light, thereby forming a reflected light. The reflected light is guided by the second optical module, and enters a third optical path provided by the third optical module 5 and will be analyzed by the image analysis module 6. Herein, a cross-sectional shape of the reflected light is defined as a second pattern according to the transmission order that the reflected light is transmitted through each optical path, wherein the cross section of the reflected light is obtained after the analysis of the image analysis module 6. The image analysis module 6 determines the curvature of the thin film 4 according to the characteristic of the second patterns. Each module of the apparatus for measuring the curvature of the thin film will be described in more detail in the following description.

The light emitting module 1 emits the single laser to be used as the incident light. The cross-sectional shape of the incident light is a first pattern. In this embodiment, the single laser emitted by the light emitting module 1 may be a gas laser or a solid-state laser, and the laser has a wavelength range of visible wavelength. The present disclosure is not limited thereto.

The first optical module 2 may be configured by a plurality of optical components to form a first optical path. When the incident light is transmitted through the first optical path, a cross-sectional shape of the incident light may be adjusted by the plurality of optical components. The plurality of optical components may be at least one single slit device or double silt device. The second optical module 3 provides the second optical path, and the function of the second optical path is similar to that of the first optical path. While the second optical path is further used for guiding the incident light transmitted along the first optical path to be incident to the thin film 4, and guiding a reflected light by the thin film 4 to enter the third optical path provided by the third optical module 5. The third optical module 5 provides a third optical path so that the reflected light passing through the second optical path may be transmitted along the third optical path. The function of the third optical path is similar to that of the first optical path. In this embodiment, the thin film 4 may be a light emitting diode (LED) wafer, but the present disclosure is not limited thereto.

The image analysis module 6 determines the curvature of the thin film 4 according to at least one characteristic of the second pattern. In this embodiment, the image analysis module 6 may be a central processing unit (CPU) or a microcontroller unit (MCU), but the present disclosure is not limited thereto. The image analysis module 6 further includes a charge-coupled device (CCD) or a complementary metal oxide semiconductor (CMOS) to capture the reflected light. Precisely, the thin film is not sure to be an ideal plane, for example, when the thin film 4 is concave or convex, the cross-sectional shape of the reflected light will be formed by the cross-sectional shape of the incident light. And during the process of the thin film 4 forming the reflected light, the cross-sectional shape of the incident light will enlarge, shrink, skew or distort correspondingly to the curvature of the thin film 4.

In other words, the cross-sectional shapes of the incident light and the reflected light will be different because of the curvature of the thin film 4. Under the condition that the thin film 4 has different curvatures, different cross-sectional shapes of the reflected light will be formed correspondingly. Therefore, the characteristic of the second pattern will change according to the different curvatures. According to a corresponding relationship between the characteristic of the second pattern and the curvature of the thin film, the image analysis module 6 derives reversely and determines the unknown curvature of the thin film 4 by measuring the characteristic variation of the second pattern. Each of the patterns has a different definition corresponding to the characteristic of the pattern. For example, the characteristic of the second pattern may be at least one of a length variation, a width variation, a ratio variation of length versus width, a diagonal variation and so on different axis after a single slit device passing through the first optical module 2.

In one embodiment, the image analysis module 6 may determine the curvature of the thin film 4 according to a plurality of different groups of standard data and the second pattern of the reflected light captured by the image analysis module 6. The plurality of different groups of standard data are predetermined data, for example, obtained from an experiment. Each group of standard data corresponds to a specific curvature of the thin film 4. Precisely, each group of standard data may comprise a substrate data and a characteristic data. Wherein, the substrate data relates to a curvature of standard substrate. In one embodiment, the substrate data may indicate that the substrate data relates to a thin film having a specific curvature and being formed by a silicon substrate, or relates to a thin film having another specific curvature and being formed by a sapphire substrate. The characteristic data relates to the characteristic of the second pattern. For example, when the first pattern is a similar rectangle, its corresponding characteristic data of second pattern may indicate the length, the width, the diagonal of the similar rectangle, or any characteristic sufficiently representing the similar rectangle. Therefore, the standard data is for indicating that when a standard substrate made of a specific material has a specific curvature, its corresponding second pattern has an aforementioned characteristic. In another embodiment, when the first pattern is an ellipse, the characteristic data of its corresponding second pattern may indicate the major axis, the minor axis, or the ratio of major axis versus minor axis of the ellipse, or any characteristic sufficiently representing the ellipse.

In this embodiment, the image analysis module 6 may obtain the characteristic data related to the thin film by analyzing the second pattern. The image analysis module 6 may compute the curvature of the thin film according to the plurality of the groups of known standard data including the substrate data and the characteristic data, and the characteristic data of the thin film. The computing schema for the curvature of the thin film may be by an interpolation method, or an extrapolation method or according to a corresponding algorithm designed by a mapping relationship between the curvature and the second pattern. For example, using known information to design a regression calculation model. Such a computing schema may be designed freely, and will be apparent to those skilled in the art. The scope of the present disclosure is not limited thereto.

The spirit of the present disclosure is that an incident light having a specific cross-sectional shape is incident to the thin film and reflected by the thin film, thereby generating a reflected light, wherein a cross-sectional shape of the reflected light has the second pattern. The image analysis module 6 determines the curvature of the thin film 4 according to the characteristic of the second pattern and a plurality of standard data. The aforementioned embodiments describe the functional blocks of the apparatus for measuring the curvature of the thin film. The embodiments of the present disclosure will further describe implementation schemas thereof as follows.

Figure 2:
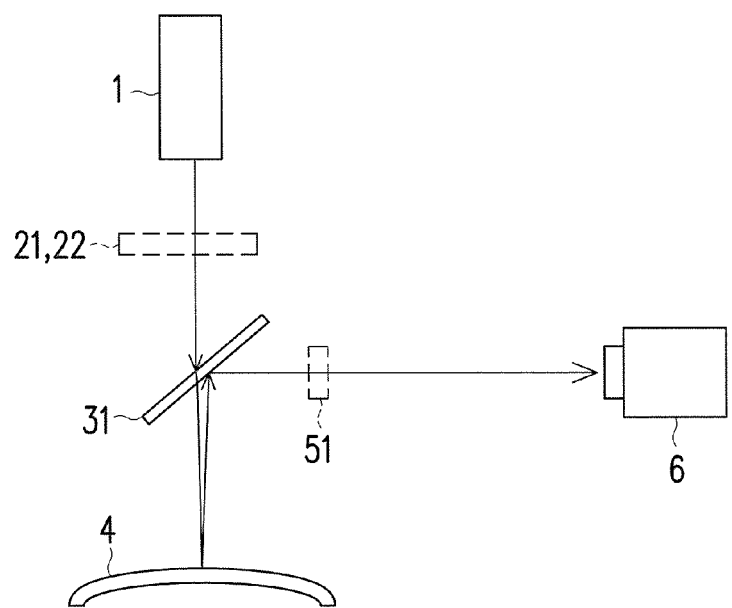
FIG. 2 is a first embodiment of the apparatus shown in FIG. 1, for measuring the curvature of the thin film.

FIG. 2 is an apparatus for measuring the curvature of the thin film according to one embodiment of the disclosure. In this embodiment, it shows a practical optical device representing each of the functional blocks shown in FIG. 1. As shown in FIG. 2, the first optical module 2 comprises a slit device 21 to form the first optical path, to have the incident light passing through the slit device 21 in the first optical path. The second optical module 3 comprises a beam splitter 31 to form the second optical path, to have the incident light passing through the beam splitter 31 in the second optical path. The incident light is reflected by the thin film 4 in the second optical path and is guided by the beam splitter 31 to enter the third optical path. Third optical module 5 comprises a first filter 51 to form the third optical path, to have the reflected light passing through the first filter 51 in the third optical path.

In one embodiment, the single slit device 21 is used to have the laser light generating a single-slit diffraction when the laser light is transmitted, thereby the cross-sectional shape of the incident light having a first pattern of specific characteristic such as a single ellipse or a similar rectangle. In another embodiment, the first optical module 2 is comprises a double slit device 22. The double slit device is used to have the laser light generating a double-slit diffraction when the laser light is transmitted, thereby the cross-sectional shape of the incident light having a first pattern of specific characteristic such as a plurality of ellipses or similar rectangles. Therefore, it may be seen that the first optical module 2 and the first filter 51 shown in FIG. 2 are used to slightly tune the shape size of the cross-section of the incident light or the reflected light. The first surface of the beam splitter 31 is used for transmitting the incident light, and a second surface of the beam splitter is used for reflecting the reflected light. Therefore, it may be seen that the second optical module 3 composed of the beam splitter 31 used for controlling the axis of the incident light and the reflected light to have the incident light and the reflected light being redirected to the desired angle and being transmitted in the desired optical path.

Referring to FIG. 1 and FIG. 2, in the embodiment of FIG. 2, the light emitting module 1 emits a single laser to be used as an incident light. As aforesaid, the incident light passes through the first optical path provided by the first optical module 2 and then the second optical path provided by the second optical module 3, wherein the incident light and reflected light are further guided by the second optical module 3 and changed the transmission axis. The image analysis module 6 receives the reflected light at the end side of the third optical path, and captures the second pattern for the reflected light. The image analysis module 6 analyzes and determines the curvature of the thin film 4 according to at least one characteristic of the second pattern and a plurality of aforesaid standard data.

Figure 3:
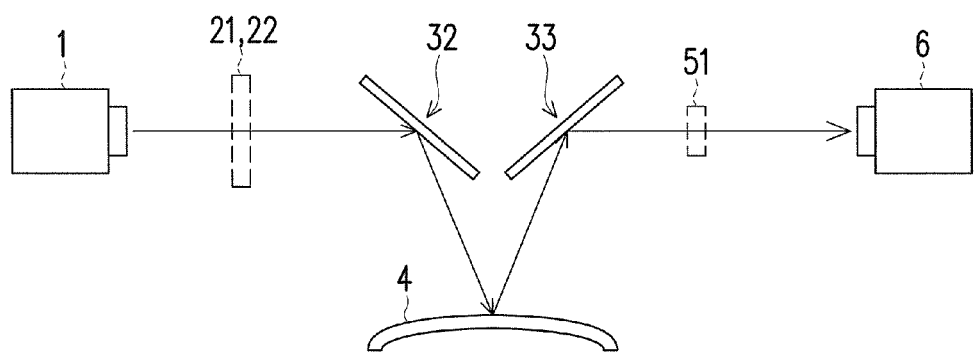
FIG. 3 is a second embodiment of the apparatus shown in FIG. 1, for measuring the curvature of the thin film.

FIG. 3 is an apparatus for measuring the curvature of the thin film according to another embodiment of the disclosure. In FIG. 3, the first optical module 2 comprises a slit device 21 to form the first optical path. The second optical module 3 comprises a first full-reflection mirror 32 and a second full-reflection mirror 33 to form the second optical path. The third optical module 5 comprises a first filter 51 to form the third optical path. The incident light is transmitted in the first optical path, then enters the second optical path. The incident light is further reflected by the first full-reflection mirror 32 in the second optical path and then is incident to the thin film 4. The reflected light from the thin film 4. The reflected light will be reflected by the second full-reflection mirror 33, then enters the third optical path. Next, as aforementioned, the image analysis module 6 receives the reflected light at the end side of the third optical path, and the second pattern for the aforesaid reflected light.

FIG. 2 and FIG. 3 respectively show an apparatus for measuring the curvature of the thin film, according to the exemplary embodiments of present embodiment. However, the scope of the present disclosure is not limited thereto. Such schemas of optical paths formed by the optical modules are apparent to those skilled in the art, and may be designed freely according to practical requirements such as types of the thin film, mechanism design, location configuration, and so on. As aforementioned, the spirit of the present disclosure is that an incident light having a specific cross-sectional shape is formed by emitting a single laser and the incident light is incident to the thin film and reflected by the thin film, thereby generating a reflected light, wherein a cross-sectional shape of the reflected light has the second pattern. The second pattern having at least one characteristic is further captured from the reflected light. The curvature of the thin film is determined according to the characteristic of the second pattern and a plurality of standard data. The following embodiments will be described in more detail.

Figures 4A, 4B:
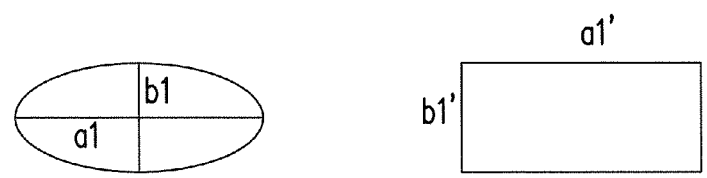
FIGS. 4A and 4B are two single second patterns corresponding to different standard data, respectively, wherein a single laser is applied and passes through a single slit device, according to one embodiment of the disclosure.

FIGS. 4A and 4B are two single second patterns corresponding to different standard data, respectively, wherein a single laser is applied and passes through a single slit device, according to one embodiment of the disclosure, wherein the second patterns are captured and analyzed by the image analysis module 6. In the embodiment of FIGS. 4A and 4B, the light emitting module 1 emits a single laser to be used as an incident light. The incident light is transmitted through the aforesaid optical paths and reflected by a convex thin film having different known curvatures. In this embodiment, the second patterns correspond to the thin film having different and known curvatures, respectively. In addition to deriving from the theorem, it may be further seen from FIGS. 4A and 4B that when the incident light of same shape is emitted through the same optical path, and is incident to the thin film having different curvatures, the corresponding reflected lights generated will have the second patterns of similar shape but different ratios, respectively.

The curvature of the thin film (for example, a wafer) is decided by a suspended height of the thin film. That is, the distance from the highest point of the thin film to a horizontal plane. Precisely, the greater the suspended height of a convex thin film is, the greater the corresponding curvature of the thin film is and the less the curvature radius of the convex thin film is. On the other side, the less the suspended height of the convex thin film is, the less the corresponding curvature of the convex thin film is and the greater the curvature radius of the thin film is. Considering the practical applications, the present disclosure uses the suspended height as a base to analyze the characteristic of the second pattern. However, as aforesaid, it may be apparent to those skilled in the art that the suspended height, the curvature, and the curvature radius are substantially interchangeable through the computation.

Referring to the embodiment of FIGS. 4A and 4B, the light emitting module 1 emits a single laser to be used as an incident light. After the incident light passes through the single slit device of the first optical module 2, the cross-sectional shape of this incident light approximates to a single ellipse or a similar rectangle under a proper distance level. When the incident light having the cross-sectional shape of single ellipse or similar rectangle is reflected by the convex thin film having a known suspended height, the length (a1, a1') and the width (b1, b1') of the cross-sectional shape of the single ellipse or similar rectangle will reduce or enlarge correspondingly. Therefore, the cross-sectional shape of the reflected light is still a single ellipse or similar rectangle, but the length and the width of the cross-sectional shape of the reflected light are different from those of the cross-sectional shape of the incident light. Also, each cross-sectional shape of the reflected light corresponds to a different curvature of the convex thin film 4. Therefore, these different second patterns are as shown in FIGS. 4A and 4B, respectively.

The present disclosure relates to an apparatus for measuring the curvature of the thin film. When the curvature of a thin film is unknown (that is, the suspended height or the curvature of the thin film is unknown), the image analysis module 6 captures and analyzes a second pattern of single ellipse or similar rectangle corresponding to the thin film having the unknown suspended height. The image analysis module 6 may compare the second pattern of similar rectangle corresponding to the unknown suspended height of the thin film with the aforesaid second pattern of similar rectangle corresponding to the known suspended height of the thin film, and compares the corresponding relationship of such as length, width or diagonal. Then, the unknown suspended height or curvature of the thin film will be determined by the image analysis module 6 through an interpolation method or an extrapolation method, or designing an analysis algorithm according to said corresponding relationship.

The concept of analyzing the second pattern in the embodiment of FIGS. 5A and 5B is similar to that in the embodiment of FIGS. 5A and 5B. Both of them determine the suspended height of the thin film 4 according to the variation of length or shape of the second patterns on two axes. It is noted that, in the embodiment of FIGS. 4A and 4B, the curvature of the thin film 4 is determined according to the length, the width or the diagonal of the second pattern such as the similar rectangle when the single laser after passes through the single slit device. Herein, FIGS. 5A and 5B are two groups of single second patterns corresponding to two groups of different standard data, respectively, wherein a single laser is applied and passes through a double slit device, and the two groups of single second patterns also correspond to the length variation of different curvatures of the thin film according to one embodiment of the disclosure. In the embodiments of FIGS. 5A and 5B, the suspended height of the thin film is determined according to the two groups of the single second patterns. For example, the length variation among the plurality of the second patterns may be at least one variation of the major axis (a1, a2, a3), the minor axis (b1, b2, b3) or the ratio of major axis versus minor axis among the two groups of ellipses, or the length, the width, the diagonal, or the spacing variation of one of the length, the width, and the diagonal, among the two groups of similar rectangles. Therefore, the curvature or the suspended height of the thin film 4 may be measured accurately in the embodiments of FIGS. 5A and 5B too.

Figure 6:
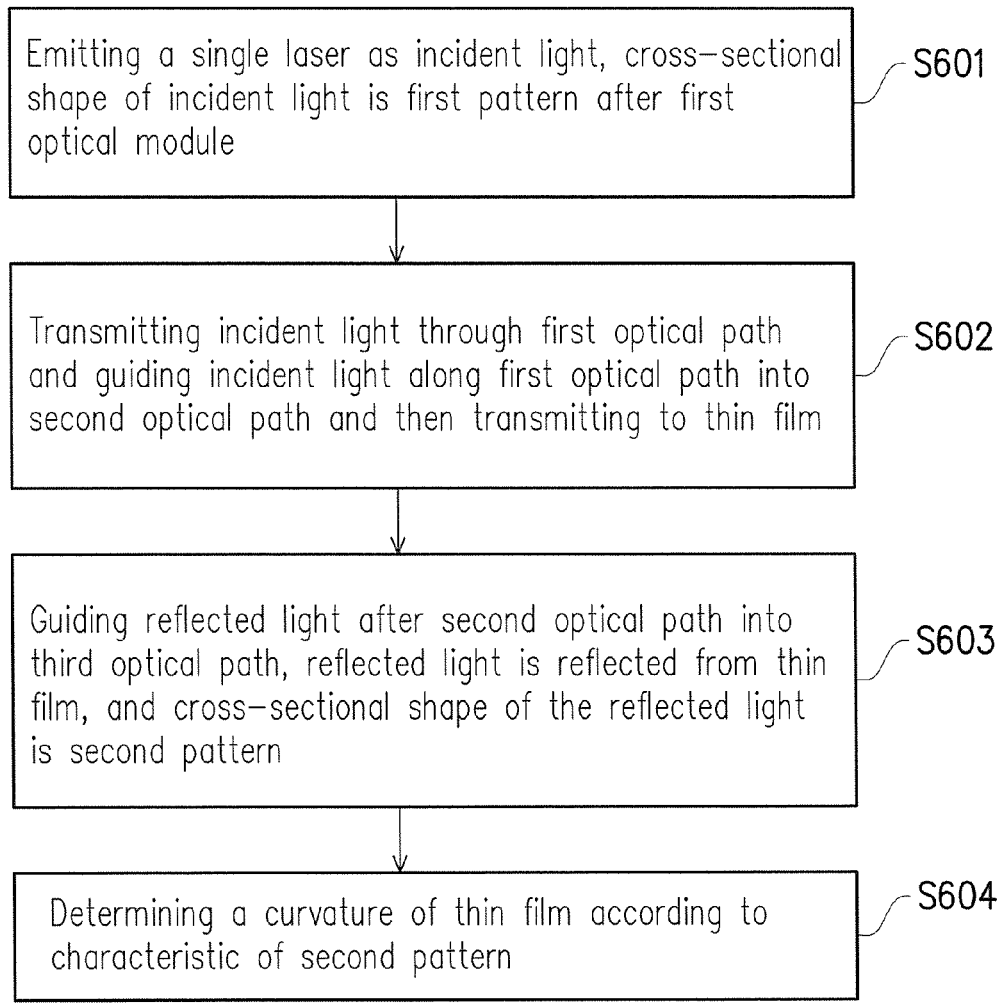
FIG. 6 is a flow chart of a method for measuring a curvature of a thin film of according to an embodiment of the disclosure.

The present disclosure also provides a method for measuring the curvature of the thin film. Referring to FIG. 6, FIG. 6 is a flow chart of the method for measuring the curvature of the thin film of according to one embodiment of the disclosure. It is noted that a first optical path, a second optical path, and a third optical path mentioned in the method may correspond to the embodiments of FIGS. 1, 2, and 3. The first optical module 2, the second optical module 3, and the third optical module 5 form the first optical path, the second optical path, and the third optical path, respectively. The method for measuring the curvature of the thin film is also applied to the aforementioned apparatus for measuring the curvature of the thin film, so also refers to FIGS. 1, 2, and 3. In step S601, a single laser is emitted to be used as the incident light. Wherein the cross-sectional shape of a first pattern is formed by at least one ellipse or similar rectangle after the incident light passes through first optical module, which also corresponds to related embodiments of FIGS. 4A-5B.

In step S602, the incident light is transmitted through a first optical path and guided the incident light transmitted along the first optical path to be incident to the thin film through a second optical path. In step S603, a reflected light passing through the second optical path is guided to enter a third optical path, wherein the reflected light is reflected from the thin film and the cross-sectional shape of the reflected light is a second pattern having at least one characteristic. In step S604, the reflected light is transmitted along the third optical path, and the reflected light transmitted to an end of the third optical path is captured. Then, a curvature of the thin film is determined according to the at least one characteristic of the second pattern.

In the aforesaid steps of the method for measuring the curvature of the thin film, the second pattern having the at least one characteristic corresponds to the embodiments of FIGS. 4A-5B. Also, after the single laser passes through the first optical module, the second pattern having the at least one characteristic comprises at least one combination of variations in length or major axis, width or minor axis, ratio of length versus width or ratio of major axis versus minor axis, and diagonal on different axes. In addition to the second pattern having the at least one characteristic, the suspended height and the curvature of the thin film may be determined according to the at least one characteristic of the second pattern of the thin film and a plurality of known standard data.

In the disclosure, an apparatus and a method for measuring a curvature of a thin film are provided. The light emitting module emits the single laser to be used as an incident light. The incident light is transmitted through a plurality of light optical paths of light optical modules, the incident light is guided to be incident to the thin film having an unknown curvature, and a reflected light formed by the reflection of the thin film is guided. Accordingly, the image analysis module determines the curvature of the thin film. Wherein, the image analysis module may determine the suspended height of the thin film according to at least one characteristic of a second pattern of the reflected light and at least one corresponding standard data. The curvature may be obtained through simple computation. As such, the apparatus and the method for measuring the curvature of the thin film may be used to monitor real-time a variation in the curvature of each wafer in the epitaxy process. This may be helpful and practical to the manufacturers to identify major factors causing the bending of the substrate are in which process, thereby adjusting and controlling corresponding process parameters to reduce the costs.

It will be apparent to those skilled in the art that various modifications and variations can be made to the disclosure.

It is intended that the specification and examples be considered as exemplary embodiments only, with a scope of the disclosure being indicated by the following claims and their equivalents.

What is claimed is:

1. An apparatus for measuring a curvature of a thin film, comprising:
a light source, emitting a single laser to be used as an incident light;
a slit device, providing a first optical path for the incident light, to have a cross-sectional shape of the incident light being a first pattern when the incident light is transmitted through the first optical path;
a beam splitter, providing a second optical path and guiding the incident light to be incident to the thin film through the second optical path, and guiding a reflected light from the thin film to enter a third optical path, wherein the cross-sectional shape of the reflected light is a second pattern;
an optical filter, providing the third optical path for the reflected light, to have the reflected light being transmitted through the third optical path; and
an image processor, capturing the reflected light and analyzing the second pattern, and determining the curvature of the thin film;
wherein the second pattern having at least one characteristic comprises at least one combination of a length variation, a width variation, a ratio variation of length versus width, a ratio variation of major axis versus minor axis and a diagonal variation on different axes.

2. The apparatus of claim 1, wherein the slit device comprises a single slit device or a double slit device, the incident light passes through the single slit device or the double slit device via the first optical path, and guided by the single slit device or the double slit device to enter the second optical path.

3. The apparatus of claim 2, wherein the beam splitter comprises a beam splitter, the incident light passes through the beam splitter in the second optical path the incident light being incident to the thin film, the reflected light reflected by the thin film is incident to the beam splitter, guided by the beam splitter and then enters the third optical path.

4. The apparatus of claim 3, wherein the optical filter comprises a first filter, the reflected light passes through, in sequence, the first filter in the third optical path, and the first filter is used to guide the reflected light to be transmitted, such that the reflected light is analyzed by the image processor.

5. The apparatus of claim 1, wherein the image processor compares and analyzes the second pattern of the cross-sectional shape of the reflected light, according to a plurality of groups of different standard data, and computes the curvature of the thin film by using an interpolation method or an extrapolation method.

6. The apparatus of claim 5, wherein each of the plurality of groups of different standard data comprises a substrate data and a characteristic data, the substrate data relates to a curvature of standard substrate, and the characteristic data relates to the second pattern of the cross-sectional shape of the reflected light.

7. The apparatus of claim 1, wherein the cross-sectional shape of the incident light passing through the slit device is an ellipse or a similar rectangle.

8. A method for measuring a curvature of a thin film, comprising:
emitting a single laser to be used as an incident light;
transmitting the incident light through a first optical path, to have a cross-sectional shape of the incident light being a first pattern when the incident light is transmitted through the first optical path;
guiding the incident light transmitted along the first optical path, to be incident to the thin film through a second optical path;
guiding a reflected light passing through the second optical path, to enter a third optical path, wherein the reflected light is reflected from the thin film, and the cross-sectional shape of the reflected light is a second pattern having at least one characteristic;
transmitting the reflected light along the third optical path, and capturing the reflected light transmitted to an end of the third optical path; and
determining the curvature of the thin film according to the at least one a characteristic of the second pattern;
wherein the second pattern having the at least one characteristic comprises at least one combination of a length variation, a width variation, a ratio variation of length versus width, a ratio variation of major axis versus minor axis and a diagonal variation on different axes.

9. The method of claim 8, wherein the incident light passes through a single slit device or a double slit device in the first optical path, and the single slit device or the double slit device is used to guide the incident light to enter the second optical path.

10. The method of claim 9, wherein the incident light passes through, in sequence, a beam splitter in the second optical path, the beam splitter is used to receive the incident light transmitted and transmit the incident light, to have the incident light being incident to the thin film, the reflected light reflected by the thin film is incident to the beam splitter, guided by the beam splitter and then enters the third optical path.

11. The method of claim 9, wherein the incident light passes through, in sequence, a first full-reflection mirror and a second full-reflection mirror, the first full-reflection mirror is used to receives the incident light transmitted, reflect the incident light, to have the incident light being transmitted and incident to the thin film, the thin film receives the incident light and redirects the reflected light, the second full-reflection mirror receives the reflected light transmitted, to have the reflected light being transmitted and entering the third optical path.

12. The method of claim 9, wherein the reflected light passes through, in sequence, a first filter in the third optical path, and the first filter is used to guide the reflected light to be transmitted, such that the reflected light is analyzed by an image processor.

13. The method of claim 10, wherein the reflected light passes through, in sequence, a first filter in the third optical path, and the first filter is used to guide the reflected light to be transmitted, such that the reflected light is captured and analyzed by an image processor.

14. The method of claim 8, wherein an image processor compares and analyzes the second pattern of the cross-sectional shape of the reflected light, according to a plurality of groups of different standard data, and computes the curvature of the thin film by using an interpolation method or an extrapolation method.

15. The method of claim 14, wherein each of the plurality of groups of different standard data comprises a substrate data and a characteristic data, the substrate data relates to a curvature of standard substrate, and the characteristic data relates to the second pattern of the cross-sectional shape of the reflected light.

16. The method of claim 8, wherein the cross-sectional shape of the incident light passing through the first optical path is an ellipse or a similar rectangle.

17. An apparatus for measuring a curvature of a thin film, comprising:
- a light source, emitting a single laser to be used as an incident light;
- a slit device, providing a first optical path for the incident light, to have a cross- sectional shape of the incident light being a first pattern when the incident light is transmitted through the first optical path;
- a reflection mirror, providing a second optical path and guiding the incident light to be incident to the thin film through the second optical path, and guiding a reflected light from the thin film to enter a third optical path, wherein the cross-sectional shape of the reflected light is a second pattern;
- an optical filter, providing the third optical path for the reflected light, to have the reflected light being transmitted through the third optical path; and
- an image processor, capturing the reflected light and analyzing the second pattern, and determining the curvature of the thin film;
- wherein the second pattern having at least one characteristic comprises at least one combination of a length variation, a width variation, a ratio variation of length versus width, a ratio variation of major axis versus minor axis and a diagonal variation on different axes.

18. The apparatus of claim 17, wherein the slit device comprises a single slit device or a double slit device, the incident light passes through the single slit device or the double slit device via the first optical path, and guided by the single slit device or the double slit device to enter the second optical path.

19. The apparatus of claim 18, wherein the reflection mirror comprises a first full-reflection mirror and a second full-reflection mirror, the first full-reflection mirror is used to receives the incident light transmitted, reflect the incident light, to have the incident light being transmitted and incident to the thin film, the thin film receives the incident light and redirects the reflected light, the second full-reflection mirror receives the reflected light transmitted, to have the reflected light being transmitted and entering the third optical path.

20. The apparatus of claim 19, wherein the optical filter comprises a first filter, the reflected light passes through, in sequence, the first filter in the third optical path, and the first filter is used to guide the reflected light to be transmitted, such that the reflected light is captured and analyzed by the image processor.

21. The apparatus of claim 17, wherein the image processor compares and analyzes the second pattern of the cross-sectional shape of the reflected light, according to a plurality of groups of different standard data, and computes the curvature of the thin film by using an interpolation method or an extrapolation method.

22. The apparatus of claim 21, wherein each of the plurality of groups of different standard data comprises a substrate data and a characteristic data, the substrate data relates to a curvature of standard substrate, and the characteristic data relates to the second pattern of the cross-sectional shape of the reflected light.

23. The apparatus of claim 17, wherein the cross-sectional shape of the incident light passing through the slit device is an ellipse or a similar rectangle.

* * * * *